(12) United States Patent
O'Neill et al.

(10) Patent No.: US 7,231,723 B1
(45) Date of Patent: Jun. 19, 2007

(54) DEVICE FOR NEURAL SENSOR PLACEMENT AND REFERENCE SYSTEM MEASUREMENTS

(75) Inventors: Kenneth R. O'Neill, Woodinville, WA (US); Richard A. Barker, Hayden Lake, ID (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/463,093

(22) Filed: Aug. 8, 2006

(51) Int. Cl.
*A61B 5/103* (2006.01)

(52) U.S. Cl. .............................. 33/512; 33/511; 33/515

(58) Field of Classification Search .......... 33/511–512, 33/515; 606/129–130
See application file for complete search history.

(56) References Cited

U.S. PATENT DOCUMENTS

| | | | |
|---|---|---|---|
| 5,423,832 | A | 6/1995 | Gildenberg |
| 6,370,414 | B1 | 4/2002 | Robinson |
| 6,413,263 | B1 | 7/2002 | Lobdill et al. |
| 2005/0055035 | A1 | 3/2005 | Cosman, Jr. et al. |
| 2005/0090756 | A1 | 4/2005 | Wolf et al. |

FOREIGN PATENT DOCUMENTS

| | | |
|---|---|---|
| EP | 0598478 B1 | 6/1999 |
| EP | 0703759 B1 | 4/2002 |
| EP | 1510182 A2 | 3/2005 |
| WO | 9320749 | 10/1993 |

OTHER PUBLICATIONS

Lapedus, Mark, "Neural-mapping chip and sensor startup emerges", EETimes.com: Semi News, printed on May 26, 2006, p. 1-2.
Clarke, Peter, "Firm demonstrates control-by-thought chip", EETimes.com: Semi News, printed on May 26, 2006, p. 1-2.

(Continued)

*Primary Examiner*—Yaritza Guadalupe-McCall
(74) *Attorney, Agent, or Firm*—Charles L. Moore; Moore & Van Allen PLLC (57) ABSTRACT

A device for at least one of neural sensor placement and taking reference system measurements may include a front frame member supportable by a person's nose when the device is placed on the person's head for at least one of neural sensor placement, taking reference system measurements or for other purposes. A pair of sidebar frame members may be attached to opposite ends of the front frame member. Each sidebar frame member may be respectively supported by one of the person's ears when the device is placed on the person's head. A back frame member includes opposite ends that may be respectively attached to each of the sidebar frame members. An angle measurement apparatus may be attached to at least one of the sidebar frame members. An arched member may be pivotably attached at one end to the angle measurement apparatus to determine an angle of the arched member relative to the sidebar frame member. An opposite end of the arched member may be attached to another of the sidebar frame members. The arched member may be adapted to arch over the person's head when the device is placed on the person's head for at least one of neural sensor placement, taking reference system measurements or for other purposes.

29 Claims, 7 Drawing Sheets

OTHER PUBLICATIONS

Weidlich, GA, Gerbert, JA, Fuery, JJ, "Clinical Commissioning of Laitinen Stereoadapter for Fractionated Stereotactic Radiotherapy", Entrez PubMed, Valley Regional Cancer Center, Modesto, CA, printed May 26, 2006, p. 1-2.

QEEG: Methodological Issues, Applied Neurosciences Group Home Page, printed Jun. 5, 2006, pp. 1-14.

Sandstrom Non-Invasive Stereodapter 5000, Sandstrom Trade & Technology, Inc., printed Jun. 5, 2006, pp. 1-3.

Laitinen, Lauri V., "Noninvasive multipurpose stereoadapter", Department of Neurosurgery, University of UD, Umd, Sweden, (1987), pp. 137-141).

DEVICE FOR NEURAL SENSOR PLACEMENT AND REFERENCE SYSTEM MEASUREMENTS

GOVERNMENT RIGHTS IN THE INVENTION

This invention was made with Government support under contract NBCH030031, awarded by the Department of the Interior/National Business Center. The Government has certain rights in this invention.

BACKGROUND OF THE INVENTION

The present invention relates to placement of sensors or the like on the human body and more particularly to a device for neural sensor placement and for taking reference system measurements, such as 10-20 coordinate or reference system measurements or reference system measurements of another measurement standard.

In collecting neurological information or similar information or data, neural sensors, such as electroencephalogram (EEG), functional near infrared (fNIR) sensors and the like, are placed on the surface of a human subject's head. These sensors typically need to be positioned accurately and repeatably with respect to some standard coordinate system. A standard known as the 10-20 coordinate system has been established for neural research. The 10-20 system allows for variation in subjects' head size and shape by specifying a reference grid relative to external head features, rather than using absolute distances. Since the 10-20 system adjusts to individual subjects, any sensor location device must also be able to adjust to individual subjects. A 10-20 grid can be laid out by measuring and marking a subject's head by hand, or by using a purpose-made stretchable cap with holes at grid intersection points. Once a grid has been laid out, locations are found relative to grid reference points by measurements along the surface of the head, and sensors are manually placed at those locations. Both of these methods require a trained and experienced operator, are time consuming, and are prone to human error. Other devices for accurately and repeatably placing sensors involve fixtures that include invasive pins or the like that are actually inserted into the human subjects scalp or skull. These devices involve extensive preparation time and skill to attach and can be extremely uncomfortable for the human subject.

BRIEF SUMMARY OF THE INVENTION

In accordance with an embodiment of the present invention, a device for at least one of neural sensor placement, taking reference system measurements or for other purposes may include a front frame member supportable by a person's nose when the device is placed on the person's head for at least one of neural sensor placement, taking reference system measurements or for other purposes. A pair of sidebar frame members may be attached to opposite ends of the front frame member. Each sidebar frame member may be respectively supported by one of the person's ears when the device is placed on the person's head. A back frame member includes opposite ends that may be respectively attached to each of the sidebar frame members. An angle measurement apparatus may be attached to at least one of the sidebar frame members. An arched member may be pivotably attached at one end to the angle measurement apparatus to determine an angle of the arched member relative to the sidebar frame member. An opposite end of the arched member may be attached to another of the sidebar frame members. The arched member may be adapted to arch over the person's head when the device is placed on the person's head for at least one of neural sensor placement, taking reference system measurements or for other purposes.

In accordance with another embodiment of the present invention, a system for at least one of neural sensor placement, taking reference system measurements or for other purposes may include an adjustable frame adapted to be non-invasively supportable by a person's head for at least one of repeatable neural sensor placement, taking reference system measurements or other purposes. The system may also include a computing device to perform at least one of a group including converting measurements from the adjustable frame to coordinates of a predetermined reference system and converting coordinates of the predetermined reference system to position adjustments on the adjustable frame.

In accordance with another embodiment of the present invention, a method for at least one of neural sensor placement, taking reference system measurements or for other purposes may include fitting an adjustable frame on a person's head. The adjustable frame may be formed to be non-invasively supportable by the person's head. The method may also include performing at least one of a group including converting measurements from the adjustable frame to coordinates of a predetermined reference system; converting coordinates of the predetermined reference system to position adjustments on the adjustable frame; or other operations.

In accordance with another embodiment of the present invention, a method for at least one of neural sensor placement, taking reference system measurements or for other purposes may include providing an adjustable frame formed to be non-invasively supportable by a person's head. The method may also include providing a computing device. The method may further include providing an application operable on the computing device to convert measurements from the adjustable frame to coordinates of a predetermined reference system; providing an application to convert coordinates of the predetermined reference system to position adjustments on the adjustable frame; or applications for other purposes.

Other aspects and features of the present invention, as defined solely by the claims, will become apparent to those ordinarily skilled in the art upon review of the following non-limited detailed description of the invention in conjunction with the accompanying figures.

DETAILED DESCRIPTION OF THE INVENTION

The following detailed description of embodiments refers to the accompanying drawings, which illustrate specific embodiments of the invention. Other embodiments having different structures and operations do not depart from the scope of the present invention.

As will be appreciated by one of skill in the art, the present invention may be embodied as a method, system, or computer program product. Accordingly, portions of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Figure 1:
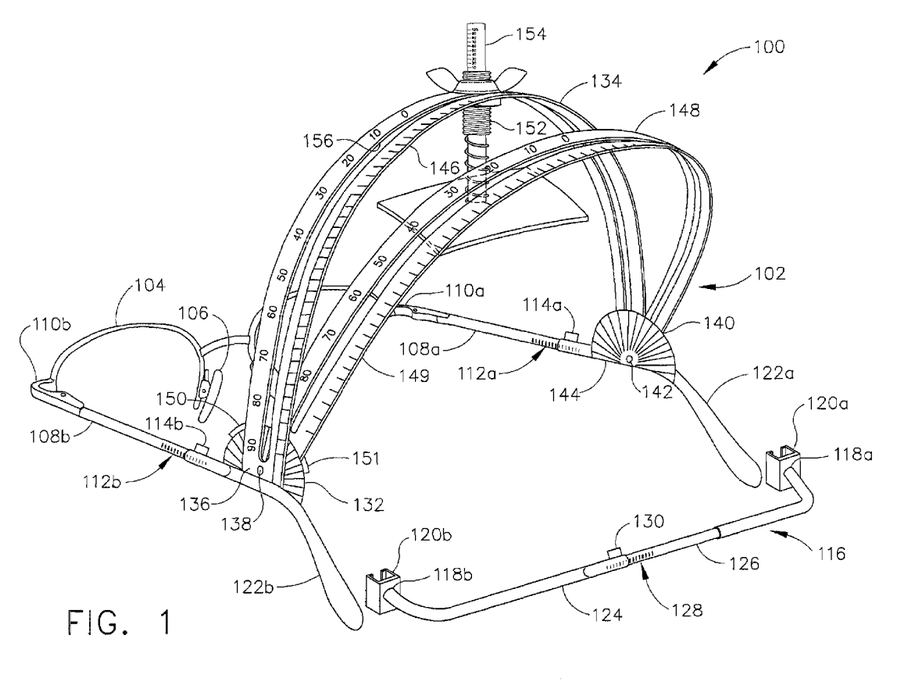
FIG. 1 is a perspective view of an example of a device for at least one of neural sensor placement, taking reference system measurements or for other purposes in accordance with an embodiment of the present invention.

FIG. 1 is a perspective view of an example of a device 100 for at least one of neural sensor placement, taking reference system measurements or for other purposes in accordance with an embodiment of the present invention. The device 100 may include an adjustable frame 102 that may be easily adjusted to accommodate different sizes of human heads. The adjustable frame 102 may substantially resemble an eyeglass frame. The device 100 or adjustable frame 102 may be formed to be non-invasively supported by a person's or subject's head.

The device 100 or frame 102 may include a front frame member 104 supportable by a person's nose when the device is placed on the person's head for at least one of neural sensor placement, taking reference system measurements or for other purposes. The front frame member 104 may substantially resemble the top half of the portion of an eyeglass frame for supporting lenses. The front frame member 104 may include nose pieces 106 for comfortably supporting the frame 102 when placed on a subject's head.

The device 100 or frame 102 may also include a pair of sidebar frame members 108 attached to opposite ends 110 of the front frame member 104. Each sidebar frame member 108 may be mounted to the front frame member 104 by a hinge similar to eyeglasses. Each sidebar frame member 108 may be respectively supported by one of the person's ears when the device 100 is placed on the person's head.

Figure 2:
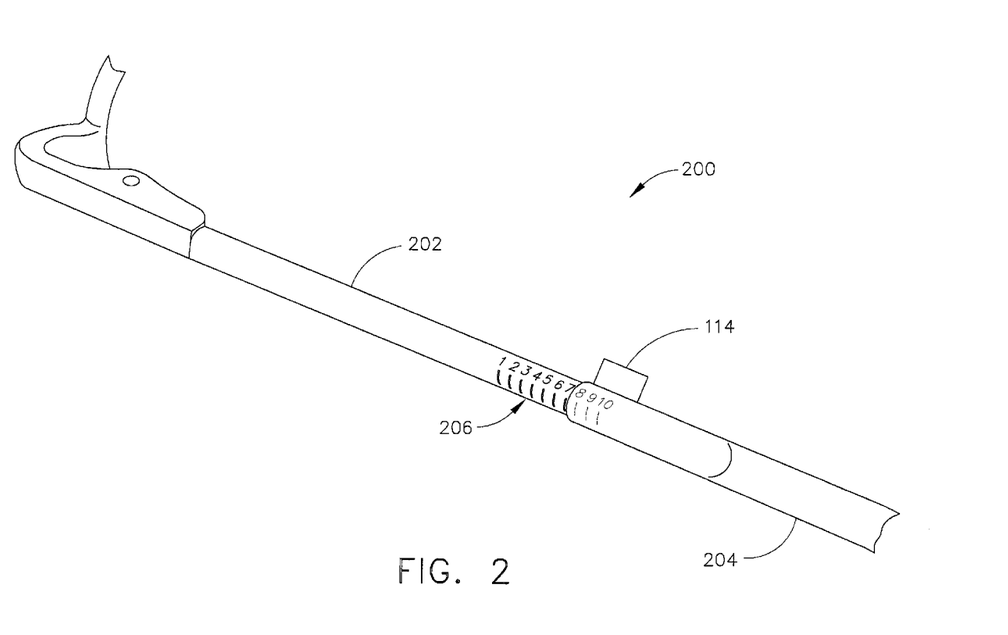
FIG. 2 is a detailed view of an example of an adjustable sidebar or earpiece of the device of FIG. 1 illustrating an indexed or numbered scale for taking reference system measurements in accordance with an embodiment of the present invention.

Each sidebar frame member 108 may have an adjustable length to accommodate different sized human heads. Referring also to FIG. 2, FIG. 2 is a detailed view of an example of an adjustable sidebar frame member 200 or earpiece that may be used for the sidebar frame member 108 of the device 100 of FIG. 1. The side bar frame member 200 may include a first portion 202 and a second portion 204. The first portion 202 and the second portion 204 may be a tube, rod, cylinder or the like. The portions or tubes 202 and 204 may be adapted to telescope, slide or adjust relative to one another to extend or contract to different lengths to accommodate different sized human heads. While the embodiment of FIG. 2 is illustrated using tubes or cylinders capable of telescoping any sort or arrangement that permits adjusting the length of the sidebar frame members 108 is contemplated by the present invention.

Each sidebar frame member 108 or 200 (FIG. 2) may also include an indexed scale 112 (or 206 as best shown in FIG. 2) to measure the adjusted position of each sidebar frame member 108 or 200. The indexed scale 112 may be a numerical scale or other type scale to facilitate conversion of measurements from the adjustable frame 102 to a predetermined coordinate or reference system or to permit position adjustments of the frame 102 from a given set of coordinates of a particular reference or coordinate system. Examples of both conversion processes will be described in more detail herein. In another embodiment of the present invention, the adjusted position of the sidebar frame members 108 may be automatically determined by a position sensor 114 or a similar device to detect the relative positions of the first and second portions 202 and 204 of each sidebar frame member 200 (FIG. 2).

The device 100 may also include a back frame member 116 including opposite ends 118 being respectively removably attachable to each of the sidebar frame members 108 to facilitate placement on a person's head located at the back of the human skull. A releasable clip 120 or similar arrangement may be attached to each end 118 of the back frame member 116 to releasably clip to a respective back end portion 122 of each sidebar frame member 108. The back frame member 116 is adapted to extend behind the subject's head and to contact the subject's inion bone. The back frame member 116 may be adapted to resist upward moments at the rear of the subject's skull.

The back frame member 116 may also include an adjustable length to accommodate different sizes of human heads. The back frame member 116 may include a first portion 124 and second portion 126 that may be adjusted relative to one another. The first portion 124 and the second portion 126 may be a tube, cylinder or similar arrangement that may telescope relative to one another to adjust the length of the back frame member 116 to accommodate different sizes of heads.

The back frame member 116 may also include an indexed scale 128 to measure the adjusted position of the back frame member 116. The indexed scale 128 may be similar to the indexed scale 112 on each of the sidebar frame members 108. The indexed scale 128 facilitates conversion of measurements from the adjustable frame 102 to a predetermined coordinate or reference system, or to permit position adjustments of the frame 102 from a given set of coordinates of a particular reference or coordinate system, as described in more detail herein.

In another embodiment of the present invention, the adjusted position of the back frame members 116 may be automatically determined by a position sensor 130 or a similar device to detect the relative positions of the first and second portions 124 and 126 of the back frame member 116. The sensor 130 may be similar to the sensors 114 associated with each of the sidebar frame members 108.

The device 100 may also include an angle measurement apparatus 132 attached to at least one of the sidebar frame members 108. As illustrated in FIG. 1, an angle measurement apparatus 132 may be attached to each of the sidebar frame members 108. The angle measurement apparatus 132 may be positioned proximate to a subject's ear when the device 100 is placed on a subject's head for at least one of neural sensor placement, taking reference system measurements or for other purposes. The angle measurement apparatus 132 may also be moveable along the side bar frame for positioning at different locations. The angle measurement apparatus 132 may be a protractor or other angle measurement means.

The device 100 may also include an arched member 134 pivotably attached at one end 136 to a center point 138 or origin of the angle measurement apparatus 132 to determine an angle of the arched member 134 relative to the sidebar frame member 108 as the arched member 134 is pivoted relative to the sidebar frame member 108. The arched member 134 may be pivotably attached at an opposite end 140 to the other sidebar frame member 108 or to a center point 142 of a second angle measurement apparatus 144. The arched member 134 is adapted to arch over the person's head when the device is placed on the person's head for at least one of neural sensor placement, taking reference system measurements or for other purposes.

The arched member 134 may also include an indexed scale 146. The indexed scale 146 may be a numerical scale with a zero marking at an apex of the arched member 134. The indexed scale facilitates conversion of measurements from the adjustable frame 102 to a predetermined coordinate or reference system, or to permit position adjustments of the frame 102 from a given set of coordinates of a particular reference or coordinate system to locate particular locations on a subject based on the particular reference or coordinate system, as described herein.

The device 100 may also include a second arched member 148. The second arched member 148 may also be pivotably attached at one end to the center point 138 of the angle measurement apparatus 132 and pivotably attached at an opposite end to the other sidebar frame member 108 or to the center point 142 of the second angel measurement apparatus 144, if provided. The angel measurement apparatus 132 may then measure an angle of the second arched member 148 relative to the sidebar frame members 108. The second arched member 148 may also include an indexed scale 149. The indexed scale 149 may be similar to the indexed scale 146 of the first arched member 134.

In another embodiment of the present invention, the angle measurement of each arched member 134 and 148 may be automatically determined by respective position sensors 150 and 151 or any type device capable of detecting the respective angle of each arched member 134 and 148 relative to the sidebar frame members 108.

The device 100 may further include a receptacle 152 for holding one of a locator rod 154, a sensor, a marker or other type device. The receptacle 152 may be adapted to slide within a slot 156 formed in the arched member 134 for location at different positions on a subject's head. A slot 158 may also be formed in the second arched member 148 and another receptacle (not shown in FIG. 1) may be slid along the slot for location at different positions. The indexed scales 146 and 149 on the first and second arched members 134 and 148 may be used to determine a position of the receptacle 152 and any type of device that may be held by the receptacle 152. The indexed scales 146 and 149 may facilitate conversion of measurements from the adjustable frame 102 and position of the receptacle 152, or device held by the receptacle, to a predetermined coordinate or reference system, or to permit position adjustments of the frame 102 and receptacle 152 from a given set of coordinates of a particular reference or coordinate system to locate particular locations on a subject based on the particular reference or coordinate system.

In another embodiment of the present invention, the position of the receptacle 152 (or any device held by the receptacle 152) along any one of the arched members 134 or 148 may be automatically determined by a position sensor 153. The position sensor 153 may be any type device capable of detecting the position of the receptacle 152 along either of the arched members 134 or 148 with which the receptacle 152 or a similar means may be used.

Figure 3:
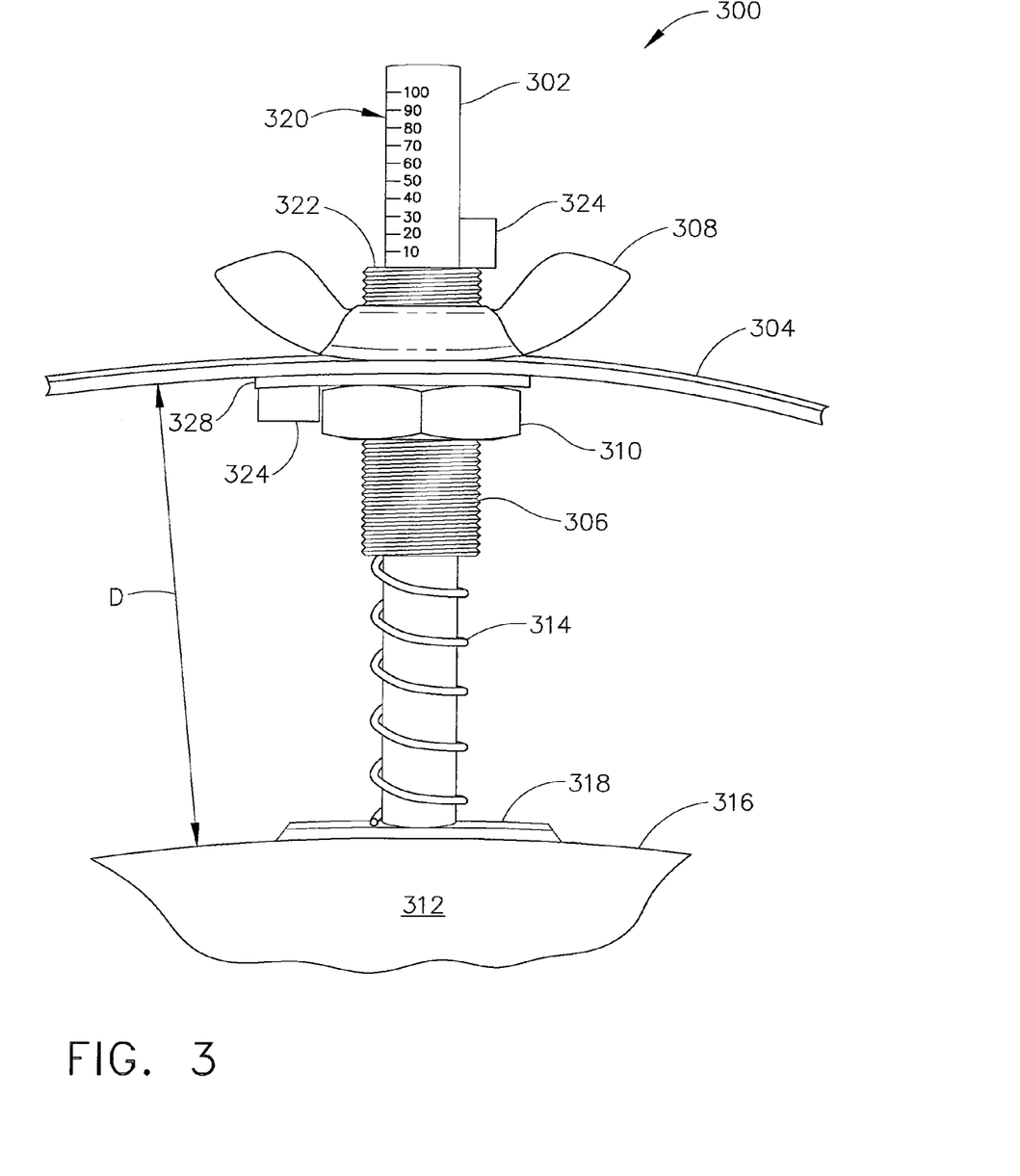
FIG. 3 is an illustration of an example of a receptacle for holding a locator rod, sensor or other device on an arch of the device of FIG. 1 in accordance with an embodiment of the present invention.

The receptacle may be any type or arrangement that may be secured or locked at a selected location along the arched member 134 or 148 relative to a subject's head and is capable of holding a locator rod, sensor, marking device or the like. FIG. 3 is an illustration of an example of a receptacle 300 for holding a locator rod 302, sensor, marking device or the like on an arched member 304 of a device similar to the device 100 of FIG. 1 in accordance with an embodiment of the present invention. The arched member 304 may be similar to arched members 134 and 148 of FIG. 1. The receptacle 300 may include a hollow bolt 306 to receive a wing nut 308 and a locking nut 310. The wing nut 308 and locking nut 310 may be tightened against one another with the arched member 304 disposed there between to lock or secure the receptacle 300 and locator rod 302, sensor, marking device or other instrument in the receptacle 300 at a selected location relative to a subject's head 312. A biasing means 314 or coil spring may urge the locator rod 302 or other instrument against the surface or scalp 316 of the subject 312. The spring insures contact with the subject 312 but allows in and out movement to accommodate different head shapes. The locator rod 302 may have a contact pad 318 attached at one end to comfortably and non-invasively contact the subject 312.

The locator rod 302 may also include an indexed scale 320. The indexed scale 320 may be similar to the other indexed scales previously described. Accordingly, the indexed scale 320 may facilitate conversion of measurements from the adjustable frame 102 to a predetermined coordinate or reference system, or to permit position adjustments of the frame 102 from a given set of coordinates of a particular reference or coordinate system. The indexed scale 320 read at a top end 322 of the hollow bolt 306 may correspond a distance "D" between the scalp 316 of the subject 312 and the arched member 304. The distance "D" together with the location of the receptacle 300 (152 in FIG. 1), as indicated by the indexed scale 146 (FIG. 1), and the angle of the arched member 134, as determined from the angle measurement apparatus 132 or protractor, establish a coordinate system that may be used by a software application as described herein to determine positions on the subject's head 312. The coordinate system may be similar to a latitude-longitude-altitude system with each of the subject's ears corresponding to a pole. The coordinate or reference system to which the device 100 may be applied may be a 10-20 coordinate or grid system. Other applicable grid or coordinate systems may include a Talairach coordinate system, Montreal Neurological Institute (MNI) coordinate system or the like.

In another embodiment of the present invention, the distance "D" between the scalp 316 of the subject 312 and the arched member 304 may be automatically determined or detected by a position sensor 324 or any type device capable of determining a relative position of the locator rod 302 within the hollow bolt 306. Similar to that previously described, another position sensor 326 or the like may automatically detect the relative position of the locator rod 302 along the arched member 304. The position sensor 326 may be similar to the position sensor 153 in FIG. 1. The position sensor 326 may held by a fixture 328 with a hole formed in one end to receive the hollow bolt 306 and to be held in place by the locking nut 310.

The arched members 134 and 148 may not be able to move past one another. Accordingly, one may become the forward arched member 134 and the other the rear arched member 148. If two sensors are needed on the same "longitude," they may be placed on the same arched member. Additional arched members may also be added if placement of additional sensors or the like may be needed.

Figure 4:
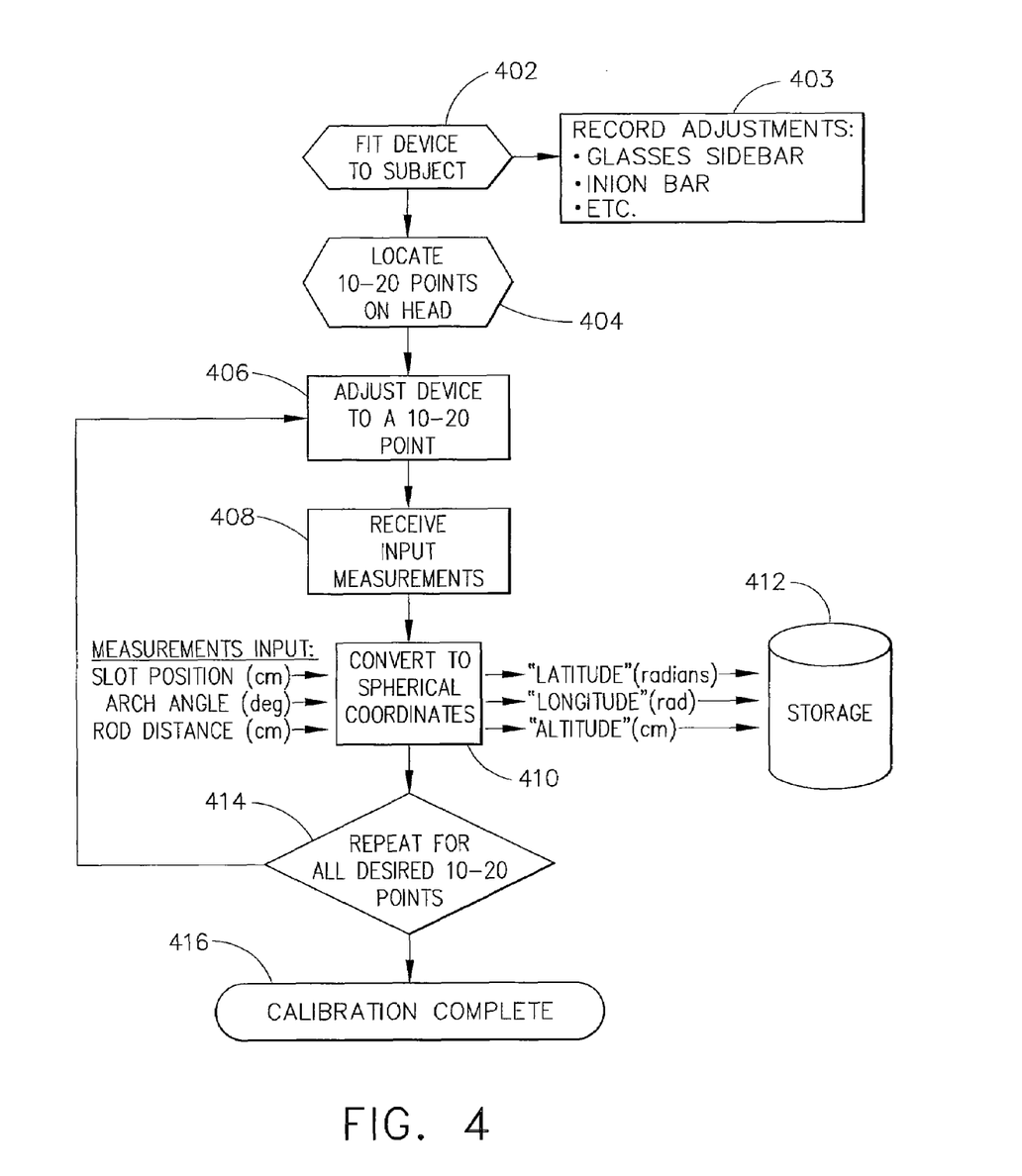
FIG. 4 is a flow chart of an example of a method for calibrating a device for one of neural sensor placement, taking reference system measurements or for other purposes in accordance with an embodiment of the present invention.

FIG. 4 is a flow chart of an example of a method 400 for calibrating a device for one of neural sensor placement, taking reference system measurements, or for other purposes in accordance with an embodiment of the present invention. The method 400 may be used in association with the device 100 of FIG. 1. In block 402, a device similar to device 100 may be fitted to a subject's head. In block 403, the sidebar frame member adjustments and positions and the back frame member or inion bar adjustments or positions from the indexed scales may be recorded.

In block 404, the 10-20 points or coordinate points of some other coordinate system may be located on the subject's head. In block 406, the device may be adjusted to a 10-20 point. In block 408, the input measurements based on the coordinate location of the 10-20 point may be received. The input measurements may include a slot position, arch angle and rod distance. The slot position may be determined from the indexed scale 146 or 149 (FIG. 1) on the arched member 134 or 148, respectively, and may be in centimeters. The arch angle may be the angle in degrees as determined by the angle measurement apparatus 132 or protractor. The rod distance may be distance "D" as determined from the locator rod 302 (FIG. 3) and may be in centimeters.

In block 410, the input measurements may be converted to spherical coordinates. The center of the spherical coordinate system may be the point midway between the two arch axels. "Latitude" in this system may be defined as zero along the centerline of a subject's head. As previously discussed, slot position may be measured in centimeters along the semicircular arched member and may be converted to an angle from the centerline by using the arch diameter. "Longitude" may be defined as the same as the measured arch angle, but may be expressed in radians. "Altitude" may be defined as the distance from the coordinate system center. The altitude may be computed by subtraction of the measured rod distance from the arch radius. The latitude, longitude and altitude may be stored in a storage device 412.

In block 414, the method 400 may return to block 406 and the method 400 may proceed as previously described for all of the desired 10-20 points identified in block 404. After all 10-20 points of interest have been converted to spherical coordinates, the calibration process 400 is complete and may end at block 416.

Figure 5:
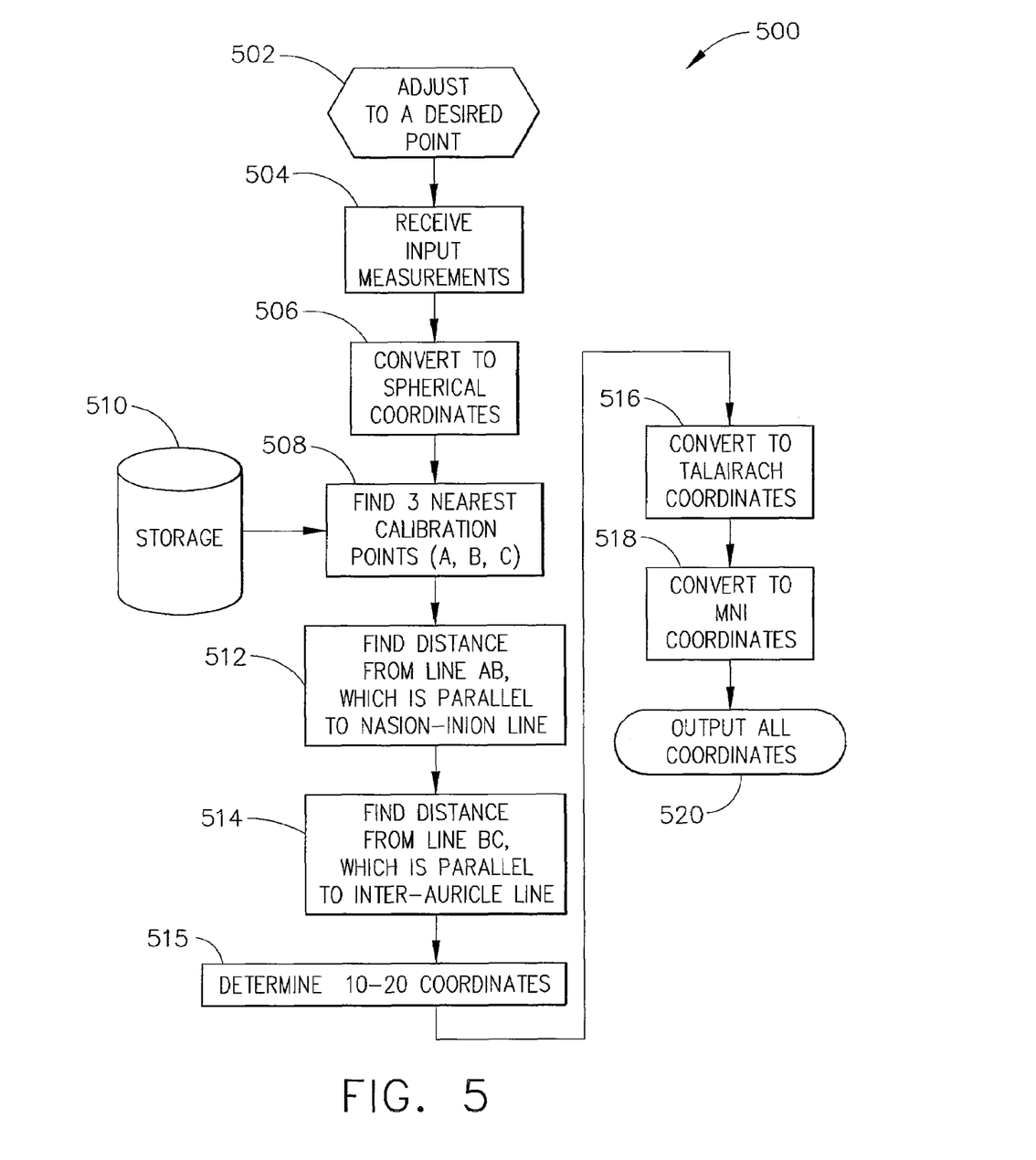
FIG. 5 is a flow chart of an example of a method for converting measurements from the device to a particular coordinate standard, convention or system in accordance with an embodiment of the present invention.

FIG. 5 is a flow chart of an example of a method 500 for converting measurements from a device, such as the device 100 of FIG. 1, to a particular coordinate standard, convention or systems in accordance with an embodiment of the present invention. In block 502, the device may be adjusted to locate a selected or desired point or position. The adjustments of the device or measurements may be determined from the indexed scales or from sensors similar to that previously described with respect to the device 100 of FIG. 1.

In block 504, the input measurements or adjustments may received or input in an application for conversion from the measurements to the particular coordinate system. In block 506, the input measurements may be converted to spherical coordinates. This conversion process may be the same or similar to that described with respect to block 410 of FIG. 4.

In block 508, the three nearest calibration points (A, B, C) may be found or determined from a storage device 510 which may be the same as storage device 412 of FIG. 4. In block 512, a distance from a line by points A and B which is parallel to a nasion-inion line or line projected between the nasion and the inion. The nasion is the intersection of the frontal bone and the two nasal bones of the human skull. The manifestation of the nasion on the visible surface of the face is the distinctly depressed area directly between the eyes, just superior to the bridge of the nose. The inion is the most prominent projection of the occipital bone at the lower rear part of the skull.

In block 514, a distance from line BC, which may be defined as parallel to the inter-auricle line may be found. The inter-auricle line may be defined as a line projected between the subject's ears. From these distances, the 10-20 coordinates may be determined in block 515. The 10-20 coordinates of the desired point may be specified as distances from the calibrated points A, B, and C. The distance computations may model the head as an ellipsoid, or use an empirically derived head shape model.

In block 516, the 10-20 coordinates may be converted to Talairach coordinates. In block 518, the 10-20 coordinates may be converted to MNI coordinates. Algorithms to perform such conversions are known in the field of neurophysiology. In block 520, the converted coordinates may be outputted or presented to a user.

Figure 6:
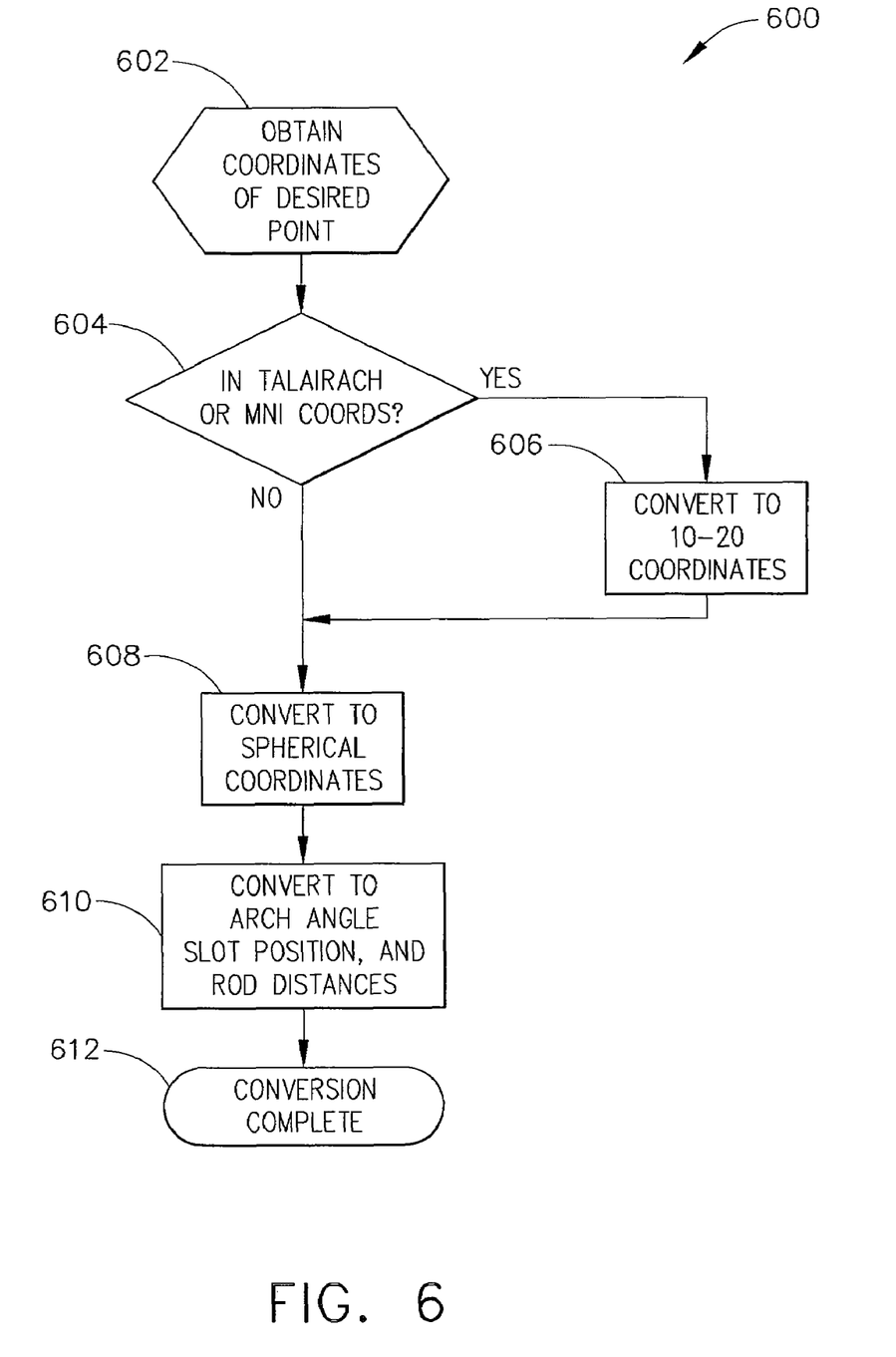
FIG. 6 is a flow chart of an example of a method for converting coordinates of a particular coordinate standard, system or convention to index locations on a device for neural sensor placement or other purposes in accordance with an embodiment of the present invention.

FIG. 6 is a flow chart of an example of a method 600 for converting coordinates of a particular coordinate standard, system or convention to index locations on a device, such as device 100 of FIG. 1, for neural sensor placement or for other purposes in accordance with an embodiment of the present invention. In block 602, coordinates of a desired point or location may be obtained. In block 604, a determination may be made if the coordinates are Talairach or MNI coordinates. If the coordinates are not Talairach or MNI coordinates or are already in 10-20 coordinates, the method 600 may advance to block 608. If the coordinates are Talairach or MNI coordinates, these coordinates may be converted to 10-20 coordinates in block 606 before the method 600 advances to block 608.

In block 608, the coordinates may be converted to spherical coordinates. In block 610, the spherical coordinates may be converted to arch angle, slot position and locator rod distances that can be used to adjust the device, such as device 100, using the index scales previously described to locate the desired point or location on the subject's head corresponding to where a rod locator (154 in FIG. 1), sensor or marking device may be positioned. The conversion will be completed in block 612.

Figure 7:
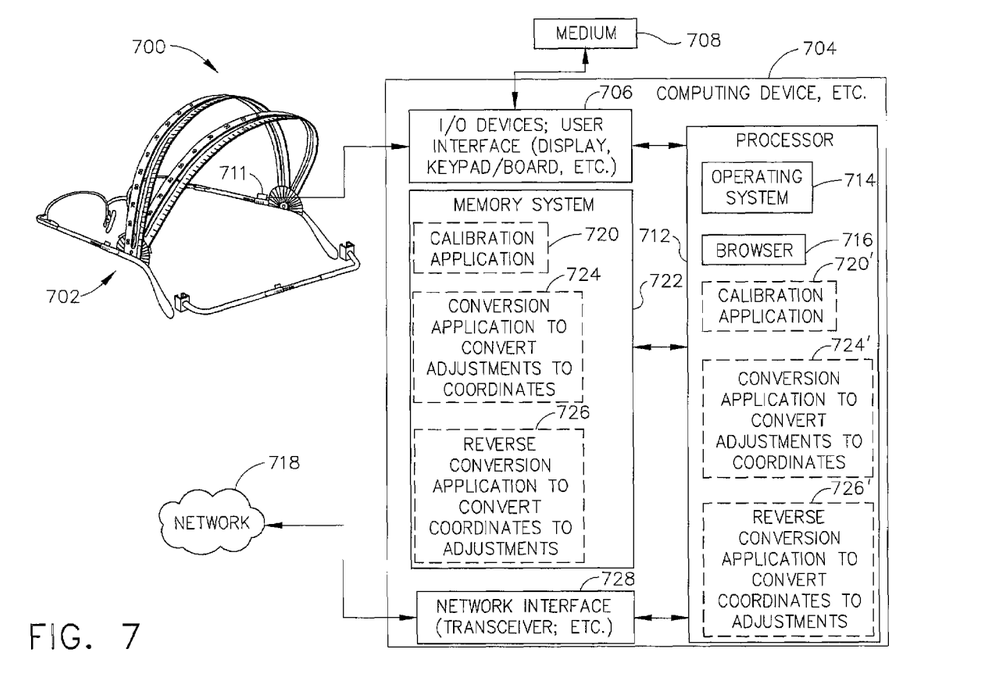
FIG. 7 is a block diagram of an example of a system for at least one of neural sensor placement, taking reference system measurements or for other purposes in accordance with an embodiment of the present invention.

FIG. 7 is a block diagram of an example of a system 700 for at least one of neural sensor placement, taking reference system measurements or for other purposes in accordance with an embodiment of the present invention. The methods 400, 500 and 600 may be embodied or performed by the system 700 or using the system 700. The system 700 may include a device 702 for at least one of neural sensor placement, taking reference system measurements or for other purposes. The device 702 may be substantially similar to the device 100 of FIG. 1.

The system 700 may also include a computing device 704 or the like. The computing device 704 may include I/O devices 706 that may be embodied as input devices, output devices or combination input/output devices. The I/O devices 706 may also include a user interface. The user interface may include a display, keyboard or keypad, pointing device or similar devices for a user to interface with the computing device 704. The I/O devices 706 may include disk drives, such as magnetic, laser, infrared or other types of data transfer devices that may receive data from a computer-usable or readable medium 708, similar to that previously described, or transmit data to the medium 708.

The I/O devices 706 may also include an interface to receive and transmit data from the device 702 for performing coordinate conversions, placing neural sensor or the like or performing other functions. The device 702 and the computing device 704 may be connected by a communications link 710 that may be wired connection, wireless connection of combination thereof. The device 702 may include a wireless transceiver 711, such as a Bluetooth transceiver or the like, to wirelessly transmit index scale measurements or position information or to receive index scale adjustments for placement of neural sensors or for other purposes.

The computing device 704 may also include a processor 712. An operating system 714 operable on the processor 712 controls operation of the computing device 704 and may control operation of various applications or other programs, such as applications related to the device 702, similar to those previously described with respect to FIGS. 4–6.

A browser 716 may also be operable on the processor for accessing web sites and other resources via a network 718. The network 718 may be the Internet, intranet or other private network.

The system 700 may include a calibration application 720 or module. The method 400 described with reference to FIG. 4 may be at least partially embodied in the calibration application 720. The calibration application may be stored in a memory system 722 and retrieved for operation on the processor 712.

The system 700 may also include a conversion application 724 or module to convert adjustments or measurements from the device 702 to coordinates of a particular reference system or coordinate system, such as 10-20 coordinates, Talairach coordinates, MNI coordinates or the like. At least some portions of the method 500 described with reference to FIG. 5 may be embodied in the conversion application 724. The conversion application 724 may be stored in the memory system 722 and then retrieved for operation on the processor 712.

The system 700 may further include a reverse conversion application 726 or module. The reverse conversion application 726 may convert coordinates of a particular coordinate system, such as Talairach, MNI, 10-20 or the like to adjustments or positions on the device 702. The reverse conversion application 726 may be also be stored on the memory system 722 and retrieved for operation on the processor 712.

The applications 724, 726 and 728 may also be a single application which performs the functions described with respect to methods 400, 500 and 600 of FIGS. 4, 5 and 6 respectively.

The computing device 704 may also include a network interface 728 for accessing the network 718. The network interface may be a transceiver or other device depending upon the nature of the network.

In summary, an adjustable framework or device is provided by an embodiment of the present invention that rests on a human subject's head and holds either a marking pen, a non-marking location indicator, a neural sensor or other device. Each adjustment of the framework moves a pointer along a scale; the resulting readout value may be entered into a software program or application operable on a computing device. The software application may compute the sensor (or marker tip) position in the 10-20 reference system or other reference system. The software application may also perform the reverse computation, producing desired adjustment values or index scale settings when given 10-20 reference coordinates or other reference system coordinates. In addition the software application may compute adjustment values when given points in two other standard reference systems, such as Talairach and MNI coordinates.

The device and system described in the various embodiments of the present invention above simplifies the process of establishing a 10-20 reference grid and recording locations relative to that grid. If the device holds a marking pen, a 10-20 grid can be quickly marked on the subject's scalp. If the device holds a non-marking indicator, that indicator can be touched to any desired location and the corresponding 10-20 coordinates can be computed. If a point is identified in a document relative to the 10-20 system, the software application can determine the framework or device adjustments that will move the indicator to that point on the subject's head. If a point is identified in Talairach or MNI coordinates, and the point is proximate the head surface, the software application can translate the point into the 10-20 system and then determine the proper adjustments.

In at least one embodiment of the present invention, the framework or device may be adapted to hold a dry-contact neural sensor, such as an Archinoetics, LLC, functional near infrared (fNIR) sensor, dry-contact electroencephalogram (EEG) sensor, a sensor from Quantum Applied Science and Research (QUASAR), Inc. of San Diego, Calif., or similar sensor. Archinoetics is a trademark of Archinoetics, LLC in the United States, foreign countries or both. An advantage of such sensors over existing wet-contact EEG sensors is that they do not require local scalp surface preparation and do not need to be attached to the head with glue. Dry-contact sensors may therefore be moved between experiments to any location on the head. The device of the present invention is adapted to take advantage of that mobility by allowing rapid, accurate placement of the sensor. The device of the present invention also allows sensor placement to be recorded and then quickly and accurately replicated in later sessions.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. A device for at least one of neural sensor placement and taking reference system measurements, comprising:
   a front frame member supportable by a person's nose when the device is placed on the person's head for at least one of a group including neural sensor placement and taking reference system measurements;
   a pair of sidebar frame members attached to opposite ends of the front frame member, each sidebar frame member being respectively supportable by one of the person's ears when the device is placed on the person's head;
   a back frame member including opposite ends being respectively attachable to each of the sidebar frame members;
   an angle measurement apparatus attached to at least one of the sidebar frame members; and
   an arched member pivotably attached at one end to the angle measurement apparatus to determine an angle of the arched member relative to the sidebar frame member and attached at an opposite end to another of the sidebar frame members, wherein the arched member is adapted to arch over the person's head when the device is placed on the person's head for at least one of the group including neural sensor placement and taking reference system measurements.

2. The device of claim 1, wherein each of the sidebar frame members comprise:
   an adjustable length to accommodate different sized human heads; and
   an indexed scale to measure the adjusted position of each sidebar frame member.

3. The device of claim 1, wherein each of the sidebar frame members comprise:
   a first tube;
   a second tube adapted to telescope relative to the first tube to accommodate different sized human heads; and an indexed scale to measure the adjusted position of each sidebar frame member.

4. The device of claim 1, further comprising a receptacle for holding one of a locator rod, a sensor and a marker, wherein the receptacle is positionable along the arched member.

5. The device of claim 4, wherein the arched member comprises an indexed scale to measure a position of one of the locator rod, the sensor and the marker along the arched member.

6. The device of claim 1, further comprising:
a receptacle positionable along the arched member;
a locator rod receivable by the receptacle;
a biasing means to urge the locator rod toward the person's head; and
an indexed scale to measure a position of the locator rod relative to the person's head.

7. The device of claim 1, wherein the back frame member comprises:
an adjustable length; and
an indexed scale to measure the adjusted position of the back frame member.

8. The device of claim 1, wherein the front frame member, each sidebar frame member and the back frame member are adjustable and wherein each of the front frame member, sidebar frame member and back frame member comprise a sensor to measure an adjusted position of each member.

9. The device of claim 8, further comprising means to transmit position information to a computing device to convert the adjusted position information to coordinates of a predetermined reference system.

10. The device of claim 9, wherein coordinates of the predetermined reference system comprise one of 10-20 coordinates, Talairach coordinates, and Montreal Neurological Institute (MNI) coordinates.

11. The device of claim 1, wherein the device is non-invasively supported on the person's head.

12. The device of claim 1, further comprising a second arched member pivotably attached at one end to the angle measurement apparatus and attached at an opposite end to the other sidebar frame member.

13. The device of claim 1, wherein the front frame member and the pair of sidebar frame members substantially resemble an eyeglass frame.

14. The device of claim 1, further comprising a sensor to automatically determine a position each member capable of adjustment to accommodate different sized heads.

15. A system for at least one of neural sensor placement and taking reference system measurements, comprising:
an adjustable frame adapted to be non-invasively supportable by a person's head for at least one of a group including repeatable neural sensor placement and taking reference system measurements; and
a computing device to perform at least one of a group including:
converting measurements from the adjustable frame to coordinates of a predetermined reference system; and
converting coordinates of the predetermined reference system to position adjustments on the adjustable frame.

16. The system of claim 15, further comprising:
an application operable on the computing device to convert measurements from the adjustable frame to coordinates of the predetermined reference system; and
another application to convert coordinates of the predetermined reference system to position adjustments on the adjustable frame.

17. The system of claim 15, wherein the adjustable frame comprises:
a front frame member supportable by a person's nose when the device is placed on the person's head for at least one of a group including neural sensor placement and taking reference system measurements;
a pair of sidebar frame members attached to opposite ends of the front frame member, each sidebar frame member being respectively supportable by one of the person's ears when the device is placed on the person's head;
a back frame member including opposite ends being respectively attachable to each of the sidebar frame members;
an angle measurement apparatus attached to at least one of the sidebar frame members; and
an arched member pivotably attached at one end to the angle measurement apparatus to determine an angle of the arched member relative to the sidebar frame member and attached at an opposite end to another of the sidebar frame members, wherein the arched member is adapted to arch over the person's head when the device is placed on the person's head for at least one of the group including neural sensor placement and taking reference system measurements.

18. The system of claim 15, wherein the adjustable frame comprises a receptacle for holding one of a locator rod, a sensor and marker, wherein the receptacle is positionable at different locations on the adjustable frame.

19. The system of claim 15, further comprising a sensor to automatically determine a position of each adjustable component of the adjustable frame.

20. The system of claim 15, further comprising means to transmit adjustment information associated with the adjustable frame to the computing device.

21. The system of claim 20, further comprising a wireless transmitter to transmit adjustment information associated with the adjustable frame to the computing device.

22. The system of claim 15, wherein coordinates of the predetermined reference system comprise one of 10-20 coordinates, Talairach coordinates, and Montreal Neurological Institute (MNI) coordinates.

23. A method for at least one of neural sensor placement and taking reference system measurements, comprising:
fitting an adjustable frame on a person's head for at least one of a group including repeatable neural sensor placement and taking reference system measurements, wherein the adjustable frame is formed to be non-invasively supportable by the person's head; and
performing at least one of a group including:
converting measurements from the adjustable frame to coordinates of a predetermined reference system; and
converting coordinates of the predetermined reference system to position adjustments on the adjustable frame.

24. The method of claim 23, wherein converting measurements from the adjustable frame to coordinates of a predetermined reference system comprises converting measurement from the adjustable frame to one of a group including 10-20 coordinates, Talairach coordinates, and MNI coordinates.

25. The method of claim 23, further comprising transmitting position information from the adjustable frame to a computing device to convert the adjusted position information to coordinates of the predetermined reference system.

26. The method of claim 23, further comprising determining a position of each adjustable component of the adjustable frame.

27. A method for at least one of neural sensor placement and taking reference system measurements, comprising:
   providing an adjustable frame formed to be non-invasively supportable by a person's head for at least one of a group including repeatable neural sensor placement and taking reference system measurements;
   providing a computing device;
   providing an application operable on the computing device to convert measurements from the adjustable frame to coordinates of a predetermined reference system; and
   providing an application to convert coordinates of the predetermined reference system to position adjustments on the adjustable frame.

28. The method of claim 27, wherein providing the adjustable frame comprises:
   forming a front frame member supportable by the person's nose when the device is placed on the person's head for at least one of the group including neural sensor placement and taking reference system measurements;
   attaching a pair of sidebar frame members to opposite ends of the front frame member, each sidebar frame member being respectively supportable by one of the person's ears when the device is placed on the person's head;
   providing a back frame member including opposite ends being respectively attachable to each of the sidebar frame members;
   attaching an angle measurement apparatus to at least one of the sidebar frame members;
   pivotably attaching an arched member at one end to the angle measurement apparatus to determine an angle of the arched member relative to the sidebar frame member; and
   pivotably attaching an opposite end of the arched member to another of the sidebar frame members, wherein the arched member is adapted to arch over the person's head when the device is placed on the person's head for at least one of the group including neural sensor placement and taking reference system measurements.

29. The method of claim 27, further comprising providing a receptacle for holding one of a locator rod, a sensor and marker, wherein the receptacle is positionable at different locations on the adjustable frame.

* * * * *